United States Patent [19]
Rokita et al.

[11] Patent Number: 5,292,873
[45] Date of Patent: Mar. 8, 1994

[54] NUCLEIC ACIDS LABELED WITH NAPHTHOQUINONE PROBE

[75] Inventors: Steven E. Rokita, Port Jefferson; Moneesh Chatterjee, Stony Brook, both of N.Y.

[73] Assignee: The Research Foundation of State University of New York, Albany, N.Y.

[21] Appl. No.: 442,947

[22] Filed: Nov. 29, 1989

[51] Int. Cl.$^5$ .............................................. C07H 21/00
[52] U.S. Cl. .................................... 536/24.3; 536/32; 548/547; 548/548
[58] Field of Search ................ 514/44, 682; 568/328; 536/27, 28, 29, 24.3, 25.32; 548/547, 548

[56] References Cited

U.S. PATENT DOCUMENTS 5,047,519 9/1991 Hobbs, Jr. et al. ................... 536/27

OTHER PUBLICATIONS

Landegren et al., "DNA Diagnostics-Molecular Techniques and Automation", *Science*, 242, 229 (1988).

Miller et al., "Oligonucleotide Inhibitors of Gene Expression in Living Cells: New Opportunities in Drug Design", *Ann. Reports in Med. Chem.*, 23, 295 (1988).

Dervan, "Design of Sequence-Specific DNA-Binding Molecules", *Science*, 232, 464–471 (1986).

Iverson et al., "Nonenzymatic Sequence-Specific Cleavage of Single-Stranded DNA to Nucleotide Resolution. DNA Methyl Thioether Probes", *J. Am. Chem. Soc.*, 109, 1241–1243 (1987).

Maher III et al., "Inhibition of DNA Binding Proteins by Oligonucleotide-Directed Triple Helix Formation", *Science*, 245, 725–730 (1989).

Tolumé et al., "Antimessenger oligodeoxyribonucleotides: an alternative to antisense RNA for artificial regulation of gene expression–a review", *Gene*, 72, 51–58 (1988).

Stein et al., "Oligodeoxynucleotides as Inhibitors of Gene Expression: A Review", *Cancer Research*, 48, 2659–2668 (1988).

Barton, "Metals and DNA: Molecular Left-Handed Complements", *Science*, 233, 727–734 (1986).

Blake et al., "Hybridization Arrest of Globin Synthesis in Rabbit Reticulocyte Lysates and Cells by Oligodeoxyribonucleoside Methylphosphonates", *Biochemistry*, 24, 6139–6145 (1985).

Agrawal et al., "Oligodeoxynucleoside phosphoramidates and phosphorothioates as inhibitors of human immunodeficiency virus", *Proc. Nat'l Acad. Sci. USA*, 85, 7079–7083 (1988).

Mori et al., "Oligodeoxynucleotide analogs with 5'–linked anthraquinone", *FEBS Letters*, 249, 213–218 (1989).

Wagner et al., "Photo-Oxidation of Thymine Sensitized by 2-Methyl-1, 4-Naphthoquinone: Analysis of Products Including Three Novel Photo-Dimers", *Photochem. Photobiol.*, 40, 589–597 (1984).

(List continued on next page.)

*Primary Examiner*—Johnnie R. Brown
*Assistant Examiner*—James O. Wilson
*Attorney, Agent, or Firm*—Hoffmann & Baron

[57] ABSTRACT

A sequence directed reagent is constructed by conjugating a methyl naphthoquinone derivative to a hexamethylamino linker attached to the 5' terminus of an oligonucleotide. Annealing this modified fragment of DNA to its complementary sequence allows for target modification subsequent to photochemical activation. The product of this reaction is a covalent crosslink between the reagent and target strands resulting from an alkylation of DNA by the photoexcited quinone. The modified sequence is not labile to acid, base or reductants, and blocks the exonuclease activity of the Klenow fragment of DNA polymerase I. In another embodiment, a highly reactive moiety, such as Br is attached to the methyl group of the naphthoquinone derivative. This reagent is similarly linked to an oligonucleotide probe. Activation of this probe linked alkylating agent is by a reductive signal which may either naturally occur within the cell, such as an enzyme, or introduced into the media containing the target molecule.

11 Claims, 3 Drawing Sheets

OTHER PUBLICATIONS

Antonini et al., "2- and 6-Methyl-1,4-naphthoquinone Derivatives as Potential Bioreductive Alkylating Agents", *J. Med. Chem.*, 25, 730–735 (1982).

Van Houten et al., "Action mechanism of ABC excision nuclease on a DNA substrate containing a psoralen crosslink at a defined position", *Proc. Nat'l. Acad. Sci. USA*, 83, 8077–8081 (1986).

Lee et al., "Interaction of Psoralen-Derivatized Oligodeoxyribonucleoside Methylphosphonates with Single-Stranded DNA", *Biochemistry*, 27, 3197–3203 (1988).

Wahl et al., "Northern and Southern Blots", *Methods Enz.*, 152, 572–573 (1987).

Higuchi et al., "DNA typing from single hairs", *Nature*, 332, 543–546 (1988).

Conner et al., "Detection of sickle cell $B^s$-globin allele by hybridization with synthetic oligonucleotides", *Proc. Nat'l. Acad. Sci. USA*, 80, 278–282 (1983).

Gamper et al., "Reverse Southern Hybridization", *Nucl. Acids Res.*, 14, 9943 (1986).

Gebeyehu et al., "Novel biotimylated nucleotide-analogs for labeling and colorimetric detection of DNA", *Nucl. Acids Res.*, 15, 4513–4534 (1987).

Jèger et al., "Oligonucleotide N-Alkylphosphoamides: Synthesis and Binding to Polynucleotides", *Biochemistry*, 27, 7237–7246 (1988).

Cocuzza, "Total Synthesis of 7-Iodo-2',3'-Dideoxy-7-Deazapurine Nucleosides, Key Intermediates in the Preparation of Reagents for the Automated Sequencing of DNA", *Tet. Letts.*, 29, 4061–4064 (1988).

Hanna et al., "Synthesis and Characterization of 5-[(-4-Azidophenacyl)thio] uridine 5'-Triphosphate, a Cleavable Photo-Cross-Linking Nucleotide Analogue", *Biochemistry*, 28, 5814–5820 (1989).

Gibson et al., "Synthesis and application of derivatizable oligonucleotides", *Nucl. Acids Res.*, 15, 6455–6467 (1987).

Bendz, in "5-Methyl-1,4-naphthaquinone. Synthesis and ultra violet absorption spectrum", *Arkiv for Kemi*, 4, 163–167 (1951).

Cameron et al., "Regioselective Bromination of 1,4-Naphthoquinones", *Aust. J. Chem.*, 34, 1513–1522 (1981).

Maniatis et al., in *J. Molecular Cloning, A Laboratory Manual*, Cold Spring Harbor Laboratory, Cold Spring Harbor, N.Y. (1982).

Cowart et al., "DNA Substrate Structural Requirements for the Exonuclease and Polymerase Activities of Procaryotic and Phage DNA Polymerases", *Biochemistry*, 28, 1975'1983 (1989).

Maxam et al., in "Sequencing End-Labeled DNA with Base-Specific Chemical Cleavages", *Methods in Enzymology*, 65, 499–560 (1980).

Becker et al., in "Use of light for footprinting DNA in vivo", *Nature*, 309, 682–687 (1984).

Martins et al., in "Photodimerization. Part V. The Conversion of 1,4-Naphthoquinones to 2,2'-Bi[1,4-Naphtoquinonyl] Derivatives Through Photodimerization and Subsequent Photo-Oxidation", *S. Afr. J. Chem.*, 30, 89–93 (1977).

J. of Med Chem, vol. 30, No. 10 pp. 1708–1709 (1987).

Scheme 2—Reductive Activation And Crosslinking

NUCLEIC ACIDS LABELED WITH NAPHTHOQUINONE PROBE

BACKGROUND OF THE INVENTION

1. Field of the Invention

This invention relates to a naphthoquinone alkylating agent that contains an oligonucleotide probe. In one embodiment the alkylating agent may be activated by light irradiation, and in another embodiment the cross-linking agent may be activated by enzymatic or chemical reduction.

2. Background of the Related Art

Currently prescribed chemotherapeutic agents acting at the level of DNA are often effective, but their therapeutic index is quite poor, limited by the lack of target specificity. An international research effort has been underway using a wide range of techniques to develop a gene specific drug—a "magic bullet" that is aimed not at an individual organism or cell type, but a single DNA sequence within a cell.

The technological advances allowing for facile DNA synthesis have produced innumerable protocols which rely on custom oligonucleotides, used as probes to screen for complementary sequences within plasmids, chromosomes and DNA libraries. See for example, Landegren et al., "DNA Diagnostics-Molecular Techniques and Automation", Science, 242, 229 (1988). The specificity of oligonucleotide hydridization has been utilized for "antisense" methods controlling selective expression of genes both in vivo and in vitro. For example, see Miller et al., "Oligonucleotide Inhibitors of Gene Expression in Living Cells: New Opportunities in Drug Design", Ann. Reports in Med. Chem., 23, 295 (1988). Sequence recognition by the binding of probes most often depends on only the non-covalent forces of hydrogen bonding formed between complementary base pairs. Complexation of this type is quite sufficient for many applications, but covalent stabilization of duplex structures could simplify many of the current protocols and provide new opportunities for processing DNA in a sequence specific manner.

Only recently introduced, the technique of oligonucleotide-directed irreversible DNA modification holds great potential as an in vitro tool for molecular biologists. See for example, Dervan, "Design of Sequence-Specific DNA-Binding Molecules", Science, 232, 464–471 (1986); and Iverson et al, in "Nonenzymatic Sequence-Specific Cleavage of Single-Stranded DNA to Nucleotide Resolution. DNA Methyl Thiolether Probes", J. Am. Chem. Soc., 109, 1241–1243 (1987). Site specificity is enforced by the hybridization of the oligomer-reactant to its complement sequence prior to drug action. Target selectivity can then be conferred, in theory, to most reactive compounds by attaching them to oligonucleotides. The required prehybridization step, however, generally limits this technique's applicability to accessible single strand polynucleotide targets or duplex probes when triple helical formation is possible, see Maher III et al., "Inhibition of DNA Binding Proteins by Oligonucleotide-Directed Triple Helix Formation", Science, 245, 725–730 (1989).

Site-directed covalent modification is also constrained by the nature of the reactive group incorporated into the oligomer. In vivo application of this method has not been demonstrated and must await the development of new reactive compounds that are compatible with a cellular environment.

Recently, messenger RNA has become a viable target for inhibiting the expression of a desired gene in vivo. See for example, Toulmé et al., "Antimessenger oligodeoxyribonucleotides: an alternative to antisense RNA for artificial regulation of gene expression—a review", Gene, 72, 51–58 (1988); and, Stein et al., "Oligodeoxyribonucleotides as Inhibitors of Gene Expression : A Review", Cancer Research, 48, 2659–2668 (1988). Compounds created for this selective reaction have drawn from the advances in site specific modification of DNA, for example see: Barton, "Metals and DNA: Molecular Left-Handed Complements", Science, 233, 727–734 (1986), and Dervan, in Science, 232 (1986) supra. Use of such compounds also depends on the synthesis of metabolically stable oligonucleotides that can transverse cell membranes. For example, see: Blake et al., "Hybridization Arrest of Globin Synthesis in Rabbit Reticulocyte Lysates and Cells by Oligodeoxyribonucleoside Methylphosphonates", Biochemistry, 24, 6139–6145 (1985). Also, see Agrawal et al., "Oligodeoxynucleoside phosphoramidates and phosphorothioates as inhibitors of human immunodeficiency virus", Proc. Nat'l. Acad. Sci. U.S.A., 85, 7079–7083 (1988).

Although a large number of reactive appendages are available for related use in vitro, as reported by Iverson et al., J. Am. Chem. Soc., 109 (1987) supra: and by Dervan, Science, 232 (1986) supra, only a limited set of these may be incorporated into techniques for in vivo use. See Mori et al., in "Oligodeoxynucleotide Analogs with 5+-linked anthraquinone", FEBS Letters. 249, 213–218 (1989) who reported the synthesis of a 5'-linked oligodeoxynucleotide in which a covalently attached group links the nucleotide to an anthraquinone molecule. The anthraquinone molecule was chosen for its potential radical-producing moiety, that does not necessarily require the presence of a metal ion or optical activation. Such a molecule, however, is incapable of alkylating the target DNA. Also, the anthroquinone probably is not photochemically active, due to the resonance structures of all of the carbon-carbon double bonds.

Wagner et al. have reported that methyl naphthoquinone sensitizes the selective oxidation of thymine, in "Photo-Oxidation of Thymine Sensitized by 2-Methyl-1,4-Naphthoquinone: Analysis of Products Including Three Novel Photo-Dimers", Photochem. Photobiol., 40, 589–597, (1984).

In an article by Antonini et al., entitled "2- and 6-Methyl-1,4-naphthoquinone Derivatives as Potential Bioreductive Alkylating Agents", J. Med. Chem., 25, 730–735 (1982). A number of antineoplastic agents which possess both a quinone nucleus and a substituent that permits them to function as bioreductive alkylating agents. Antonini et al. reported the synthesis of a series of 2-and 6-methyl-1,4-naphthoquinone derivatives, and evaluated them for antitumor effects on mice bearing Sarcoma 180 ascites cells. These antitumor agents were thought to be activated by reduction to an alkylating species. Such reduction was believed to take place due to enzymes produced by the metabolic system of hypoxic tumor cells, functioning under low oxygen tension. Antonini et al. did not, however, describe or suggest the delivery of the naphthoquinone derivatives into the cell DNA by using a target specific probe. Nor did Antonini et al. describe the modification or use of such naphthoquinones as UV activated alkylating agents. Indeed, as shown in Example 4, the structure shown in Scheme 1 of Antonini et al., with their —CH$_2$—X group on the quinone ring structure would not be practical, since it would attack and degrade a probe during the linking process. Additionally, Antonini et al. inset their —CH$_2$—X group on carbon 6 of the benzene ring, they do not, however, suggest inserting the —CH$_2$—X group on the other positions of the benzene ring.

Yabusaki et al., in PCT Published Application No. WO 85/02628 describe cross-linking agents for binding an oligonucleotide probe to a target DNA or RNA molecule. Three types of cross-linking agents are described, including "bi-functional photoreagents", "mixed chemical and biochemical bifunctional reagents" and "bifunctional chemical cross-linking molecules". The bifunctional photoreagents contain two photochemically reactive sites that bind covalently to the probe and to the target molecules. The mixed chemical and photochemical bifunctional reagent is bound non-photochemically to the probe molecule, followed by photochemical binding to the target molecule. Non-photochemical binding is described as a chemical reaction such as alkylation, condensation or additional. Bifunctional chemical cross-linking molecules are said to be activated either catalytically or by high temperature following hybridization.

Although Yabusaki et al. generally hypothesize the concept of a bifunctional photochemical reagent and a mixed chemical and photochemical reagent, there is no specific description of these molecules. All of the reagents they describe are well known photochemical reagents, these include the psoralen derivatives, including furocoumarins, the benzodipyrone derivatives, and the bis-azide derivatives. None of these molecules, however, work on the basis of reductive activation. In addition, these compounds are not practical in vivo reagents. It would be difficult or nearly impossible to photoactivate these reagents in vivo. These reagents, especially the psoralen derivatives are toxic, causing severe burning of the organism after exposure to sunlight. Finally, the covalent crosslinks formed by psoralens are not permanent, rather, they are degraded by UV irradiation.

Two recent articles reported the use or psoralen crosslinks of DNA substrates, the first by Van Houten et al., in "Action mechanism of ABC excision nuclease on a DNA substrate containing a psoralen crosslink at a defined position", *Proc. Nat'l Acad. Sci. USA*, 83, 8077–8081 (1986), and the second by Lee et al., in "Interaction of Psoralen-Derivatized Oligodeoxyribonucleoside Methyl-phosphonates with Single-Stranded DNA", *Biochemistry*, 27, 3197–3203 (1988). Both articles reported covalent crosslinking between the DNA molecule and a complementary oligomer that contains a psoralen derivative. The covalent binding of the psoralen derivative to the DNA molecule was activated by UV irradiation. Accordingly, just like the Yabusaki patent application, none of these references describe the chemically activated covalent binding agent which may be used in vivo. Additionally, as discussed above, the covalent crosslinks, formed by psoralens are not permanent, being degraded by UV irradiation.

The techniques of Northern and Southern blotting are two of the most powerful and frequently used procedures in molecular biology, see Wall et al., "Northern and Southern Blots", *Methods Enz.*, 152, 572–573 (1987). Yet the necessary manipulations are time consuming and are not likely to be automated under current technology. Often the polynucleotide (RNA, DNA) under analysis must first be fractionate by size, transferred onto a solid support and then treated through a series of steps to ensure only specific binding of a probe. Detection of the hybridized products usually depends on radiolabelling, heavy metal derivatization or antibody complexation. The methods of blotting have been a staple of basic research, and now also serve in an ever increasing number of commercial kits used to diagnose genetic malignant and infectious diseases (see Landegren et al. *Science*, 242, (1988) supra). Related advances have also allowed these processes to aid in forensic science, see Higuchi et al., "DNA typing from single hairs", *Nature*, 332, 543–546 (1988); and, the Human Genome Project, see Conner et al., "Detection of sickle cell β$^s$-globin allele by hybridization with synthetic oligonucleotides", *Proc. Nat'l Acad. Sci. USA*, 80, 278–282 (1983).

Psoralens have been used to randomly crosslink duplex DNA during hybridization in order to facilitate Southern Blotting procedures. This new test is referred to as Reverse Southern blotting. For example, see Gamper et al., in "Reverse Southern Hybridization", *Nucl. Acids Res.*, 14, 9943 (1986). Other biochemical and reduction activated reagents are needed to replace or complement psoralens for sequence detection and to provide an alternate set of conditions for duplex stabilization.

Accordingly, none of the related art describes or suggests using UV and/or visible light ("UV/Vis.") activation with a naphthoquinone derivative in order to permanently alkylate a biological molecule such as DNA.

Therefore, it is an object of the present invention to provide a new class of photochemically activated alkylating probes which form a permanent covalent crosslink.

Another object of the present invention is to provide an enzymatic or chemical reduction activated alkylating probe which can be used in vivo.

A further object of the present invention is to provide a new class of photochemical and reduction activated Reverse Southern blotting reagents for conjugating and permanently crosslinking target oligonucleotides and facilitate blotting procedures, sequence detection and scission.

SUMMARY OF THE INVENTION

These and other objects are achieved by the present invention which provides a process and composition for selectively and permanently alkylating a target molecule. The process includes the steps of providing a probe, such as an oligonucleotide, for recognizing a predetermined binding site on a target molecule, such as a DNA sequence which is complementary to the probe. Providing a 1,4-naphthoquinone derivative for linking to the probe. Linking the probe to the 1,4-naphthoquinone derivative to form a targeted alkylating agent. The targeted alkylating agent has the general formula:

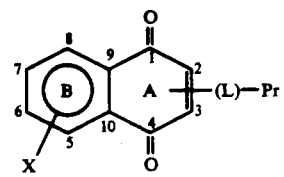

In which X is positioned on any of carbon atoms 2,3 and 5–8, L is an alkyl linking group for attachment to a probe which may be positioned at any carbon atoms on either of the A or B rings, and Pr is a probe for binding to a target molecule.

The targeted alkylating agent is then introduced into a system containing the target molecule to allow the probe to associate, i.e. hybridize, with a target molecule and localize the linked 1,4-naphthoquinone derivative near the target molecule. The targeted alkylating agent is activated by a signal which causes covalent bonding between the 1,4-naphthoquinone derivative proximal to the association site of the probe with a target molecule.

In one embodiment, the X group is a hydrogen, methyl or alkyl group and activation is by light irradiation after the targeted alkylating agent is allowed to associate with the target molecule.

In another embodiment, the X group is a displacable reactive moiety attached to an alkyl group positioned on carbon atoms 5–8 of ring B only. Examples of such groups include Br, Cl, F, I, OAc, OH, $OSO_2CH_3$, $OSO_2C_6H_4CH_3$-p $OCH_2CH_3$, $OCONHCH_3$ and $OCONHCH_2CH_2R$. In this embodiment the alkylating agent is activated by a reductive signal which either naturally occurs within the cell, through an enzyme mediated pathway, or by a signal that is introduced into the media containing the target molecule.

For a better understanding of the present invention reference is made to the foregoing description made in conjunction with the figures, the scope of which is defined in the claims.

DETAILED DESCRIPTION OF THE INVENTION

Figure 1A:
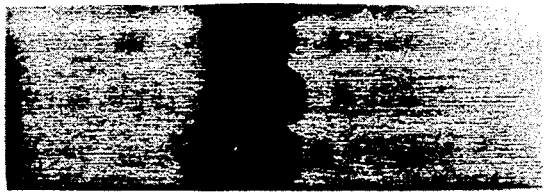
FIG. 1A shows autoradiograms of denaturing polyacrylamide gels used to identify photochemical crosslinks forms within a duplex DNA structure illustrating one embodiment of the present invention, described in Example 2.

In accordance with a preferred embodiment of the present invention a naphthoquinone derivative is conjugated to an oligonucleotide probe which has potential for selective in vivo alkylation of target biological molecules. It is believed that naphthoquinones should neither impede the cellular uptake of appropriately modified nucleotides nor react indiscriminately with DNA.

The novel naphthoquinone probe composition has the following generalized formula:

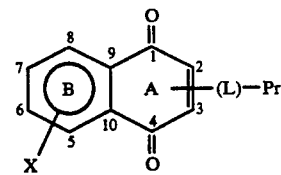

In which X is positioned on any of carbon atoms 2, 3 and 5–8, L is a linking group for attaching the naphthoquinone derivative to the probe which may be positioned at any carbon atom on either the A or B rings, and P is a probe for binding to a target molecule.

In one embodiment of the invention, the naphthoquinone probe is localized to a target molecule and alkylates the target molecule after photochemical activation by light irradiation. In this embodiment X can be H, $CH_3$ or any alkyl group.

In another embodiment, the naphthoquinone probe alkylates a target molecule after activation by a reductive signal. In this embodiment X is a leaving group $R_4$ connected to an alkyl chain positioned on carbon atoms 5–8 of ring B only. The alkyl chain is connected at one end to the B ring of a naphthoquinone molecule and requires a leaving group $R_4$ on the same carbon that connects to ring B. Thus, X has the following generalized formula:

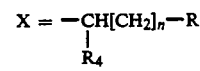

In which n is a positive integer and $R_4$ may include one of the leaving groups, such as Cl, Br, F, I, OCOR, OH, $OSO_2CH_3$, $OSO_2C_6H_4CH_3$-p, OR, OCONHR, and $OCONHCH_2CH_2R$.

In all of these compositions, the linking group L is made up of a chain $—R_1—R_2—R_3—$. Generally the $R_1$ group may include a group for linking to the naphthoquinone derivative including N, S, O or $CH_2$. The $R_2$ group can include any spacer group which can link $R_1$ and $R_3$, such as an alkyl chain. The $R_3$ group is any group which can link to a modified oligonucleotide or other probe P, examples of these are $NH_2$, SH, OH and COOH. The probe P includes any localizing moiety, such as an oligonucleotide, protein, antibody, sugar or other molecule that preferentially localizes to an organic molecule, including DNA, RNA, or protein. The oligonucleotide, whether DNA or RNA may be linked to $R_3$ at either its 5' or 3' terminus or at an intermediate position in the nucleotide polymer.

Alternatively, the oligonucleotide may be linked to $R_3$ at any oligonucleotide base, or phosphoribose backbone suitably modified in accordance to the methods described by the following publications, the disclosure of which is incorporated by reference herein:

1. Gebehehu et al., "Novel Biotinylated nucleotideanalogs for labelling and colorimetric detection of DNA", *Nucl. Acids Res.*, 15, 4513–4534 (1987).

2. Jàger et al., "Oligonucleotide N-alkylphosphotamides: Synthesis and Binding to Polynucleotides", *Biochemistry*, 27, 7237–7246 (1988).

3. Cocuzza, "Total Synthesis of 7-Iodo-2', 3'-Dideoxy-7-Deozopurine Nucleosides, Key intermediates in the Preparation of Reagents for the Automated Sequencing of DNA", *Tet. Letts.*, 29, 4061–4064 (1988).

4. Hanna et al., "Synthesis and Characterization of 5-[(4-Azidophenacyl)thio]uridine 5'-Triphosphate, a Cleavable Photo-Cross-Linking Nucleotide Analogue", *Biochemistry*, 28, 5814–5820 (1989).

5. Gibson et al., "Synthesis and Application of Derivatizable Oligonucleotides", *Nucl. Acids Res.*, 15, 6455–6467 (1987).

In one preferred embodiment of the invention, described in examples 1 and 2, the alkylating naphthoquinone probe is activated by light, preferably UV irradiation. In this embodiment X is a methyl group positioned at the 5 carbon of the B ring, and the linking group L is an N-hydroxysuccinimide ester of this (5-Methyl-1,4-naphthoquinonyl thio)-propionic acid which is linked to a DNA strand at its 5' terminus.

The present invention also describes a process for selectively alkylating a target molecule. A great number of useful clinical and laboratory applications for which this process may be applied are described for somewhat related processes in PCT published Application No. WO 85/02628 to Yabusaki et al., and in article by Antonini et al., *J. Med. Chem.*, 25, 730–735 (1982). The disclosure of both publications is incorporated by reference herein. Also the process of Reverse Southern Blotting is described generally in the Background of the Related Art, supra.

Generally, the process of this invention is carried out by first providing a probe for recognizing a predetermined binding site on a target molecule. The probe may include a strand of DNA, RNA, or a protein; or it may include any other molecule which can localize the probe to a target molecule. The process is carried out by providing a 1,4-naphthoquinone derivative which is modified for linking to the probe molecule. The probe is then linked to the 1,4-naphthoquinone derivative to create a targeted alkylating agent. The target alkylating agent is introduced into a system containing a target molecule and the probe associates with the target molecule localizing the linked 1,4-naphthoquinone derivative near the target molecule. Crosslinking or covalent bonding is then initiated by activating the targeted alkylating agent by either a reductive signal or light irradiation. A covalent bond is then formed between the 1,4-naphthoquinone derivative and the target, proximal to the association site of the probe with the target molecule.

In one preferred embodiment, the linking step derivative by the addition of an acidic linking group which is capable of being modified for linking to the probe molecule. Preferably, this adapting step is a Michael addition reaction of 3-mercaptopropionic acid, which is then followed by activation of the acid by esterification with N-hydroxysuccinimide. In some embodiments, the 1,4-naphthoquinone derivative includes an arm attached to the B ring, preferably methyl ($CH_3$), but it may also include any alkyl group —$(CH_2)_n$—R where n is a positive integer. In these embodiments, the step of activating alkylation and covalent bonding between the associated probe and target molecule is carried out by light irradiation.

If the arm attached to the B ring includes a reactive leaving group, such as bromomethyl or any of the other leaving groups described, supra, activation is carried out by a reductive signal, such as reduction by an enzyme in a cell containing the target molecule; or, by the introduction of other reducing agents, such as sodium borohydride, dithionite, sodium cyanoborohydride, and thiols, in vitro.

Preferably, if reductive activation is desired the adapting step of adding a carboxyl linking group is followed by a bromination step which replaces one of the hydrogen atoms on the alkyl, preferably methyl, arm with a bromine atom. If leaving groups other than bromine are desired, the bromination step may be followed by a substitution of the bromine with other leaving groups such as Cl, F, I, OCOR, OH, $OSO_2CH_3$, $OSO_2C_6H_4CH_3$-p, OR, OCONHR, and $OCONHCH_2CH_2R$.

It is believed, however, that the alkyl arm carrying the leaving group can only be placed on the B ring of the 1,4-naphthoquinone derivative. Attempts to place a brominated leaving group on the A ring resulted in the probe being attacked and degraded by the highly reactive methyl bromine arm, as described in example 4.

The process of this invention, with reductive activation may be carried out in vivo, and the activation may be triggered by an enzyme catalyzed reduction within the organism that contains the target molecule.

If in vivo use is desired, then suitably modified probes that are capable of transversing cell membranes are prepared, for example as described by Blake et al., "Hybridization Arrest of Globin Synthesis in Rabbit Reticulocyte Lysates and Cells by Oligodeoxyribonucleoside Methylphosphonates", *Biochemistry*, 24, 6139–6145 (1985); and, by Agrawal et al., "Oligodeoxynucleoside phosphoramidates and phosphorothioates as inhibitors of human immunodeficiency virus", *Proc. Nat'l. Acad. Sci. U.S.A.*, 85, 7079–7083 (1988). These probes are then attached to activated esters 2a–2i, respectively. Alternatively, a reductive signal may be selectively introduced in order to trigger alkylation and crosslinking.

For example, in mice attacked by cancer cells, as reported by et al., (1982), supra, hypoxic tumor cells create a reducing environment for enzymes which in turn cause reduction and thereby selectively trigger similar naphthoquinone derivatives having reactive leaving groups. Antonini et al., however, did not target their naphthoquinone derivative by using a probe of any kind.

The process of this invention, of course, can be carried out in vitro using either reductive or photochemical activation. In fact, photochemical activation may even be used in vivo by introducing a UV/Vis. transmitting fiber optic filament into the organism through a needle or catheter for site specific activation of crosslinking.

The following examples further illustrate the various features of the invention, and are not intended in any way to limit the scope of the invention which is defined in the appended claims.

In Examples 1 and 2, we have shown that a preferred probe, as described above, bearing the methyl naphthoquinone derivative of the present invention causes selective alkylation of a DNA target, which has been photochemically activated after the probe has hybridized with the target DNA sequence.

EXAMPLE 1

Preparation of a Photochemically Activated Alkylating Methylnaphthoquinone Linked Probe A photochemically activated alkylating methylnaphthoquinone linked probe was prepared in accordance with the invention. The probe was tested in vitro using a synthetic DNA target strand. The steps followed in the synthesis of the UV activated alkylating probe are shown in Scheme 1.

thoquinones", *Aust. J. Chem.*, 34, 1513–1532 (1981), which were carried together throughout the following procedures. The acid 1 was then treated with N-

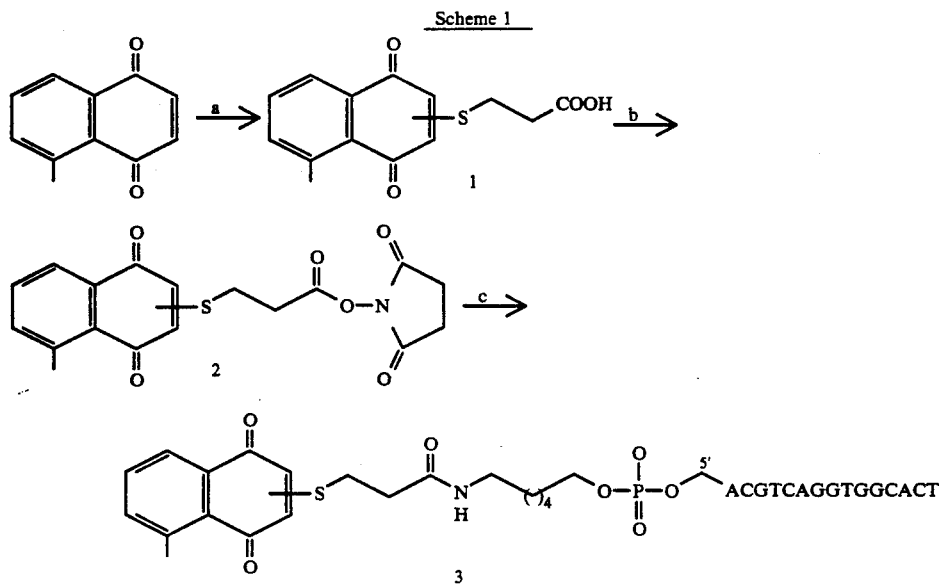

(a) 3-mercaptopropionic acid, 70% EtOH, 4° C.; (b) N-hydroxysuccinimide, 1-ethyl-3-(3-dimethylaminopropyl)- carbodilmide, DMF, 4° C.; (c) Oligo-(CH₂)₆-NH₂, 3-(N-morpholino)-propanesulfonic acid (MOPS), pH 7.5, 50% DMF, 4° C.

As shown in Scheme 1, 5-Methyl-1,4-naphthoquinone was synthesized as described by Bendz, in "5-Methyl-1,4-naphthoquinone. Synthesis and ultra violet absorption spectrum", Arkiv för Kemi, 4, 163–167 (1951). The 5-methyl 1,4-naphthoquinone was then condensed with 3-mercaptopropionic acid, in accordance with protocol 1, to yield 5-methyl-1,4 naphthoquinonyl thio)-propionic acid which provides a convenient point of attachment to an oligonucleotide probe.

Protocol 1, for preparing (5-methyl-1,4 naphthoquinonyl thio)- propionic acid 1, the Michael addition product of 3-mercaptopropionic acid and 5-methyl-1,4-naphthoquinone 3-Mercaptopropionic acid (0.69 mmol, 65 μL) was dissolved in 8 mL of water and cooled in an ice bath. This solution was added over 20–30 minutes to a solution of 5-methyl-1,4-naphthoquinone (0.69 mmole, 120 mg) dissolved in 15 mL of ethanol and cooled in an ice bath to form a reaction mixture. The reaction mixture was gradually allowed to warm to room temperature over a 1 hour period, and the ethanol was then allowed to evaporate. The crude product was purified via flash silica column chromatography (2:1 hexane:ethyl acetate with 1% v/v acetic acid) and provided a 70% yield of (5-methyl-1,4 naphthoquinonyl thio)- propionic acid, designated compound 1. $^1$H NMR data: (acetone-d$_6$), δ 2.70 (s, 3H), 2.81 (t, J=7.2 Hz, 2H), 3.20 (t, J=7.2 Hz, 2H), 6.72 (s, 1H), 7.62 (d, J=7.5 Hz, 1H), 7.71 (t, J=7.5 Hz, 1H) 7.96 (d, J=Hz, 1H). LRMS m/z (rel. int.) 276 (M+, 30.5) 203 (100), 115 (68.2), 90 (41.0), 89 (76.4).

The products of this reaction, were two inseparable acid regioisomers of (5-methyl-1,4 naphthoquinonyl thio)-propionic acid 1, as generally described by Cameron et al., "Regioselective Bromination of 1,4-Naphhydroxysuccinimide in the presence of 1-ethyl-3(3-dimethylaminopropyl)-carbodiimide in accordance with protocol 2 to yield the activated N-hydroxysuccinimide ester of (5-methyl-1,4-naphthoquinonyl thio)-propionic acid 2.

Protocol 2, for the activating the acid 1 to yield the activated ester 2

N-hydroxysuccinimide (72 μmol, 8.3 mg.) and the acid 1 (72 μmol, 20 mg) were dissolved in 80 μL of DMF and cooled in an ice bath. 1-Ethyl-3-(3-dimethylaminopropyl)-carbodiimide (72 μmol, 13.8 mg) was added, mixed once and then placed at 4° C. overnight. During this time the product precipitated out. Two (2) mL of water were added to complete the precipitation. The crude product was isolated by centrifugation and washed with 100 mM potassium phosphate buffer (pH 7.5) to remove unreacted starting material. The precipitate was then further washed with water, dried under high vacuum and purified via flash silica column chromatography (2:1 hexane:ethyl acetate) to yield 81% of the activated N-hydrosuccinimide ester of (5-methyl-1,4-naphthoquinonyl thio)-propionic acid, designated as compound 2. $^1$H NMR data: (CD$_3$CN), δ 2.74 (s, 4H), 2.86 (s, 3H), 3.07 (t, J=7.2 Hz, 2H), 3.19 (t, J=7.2 Hz, 2H), 6.61 (s, 1H), 7.51 (d, J=7.5 Hz, 1H), 7.71 (t, J=7.5 Hz, 1H), 8.03 (d, J=7.5 Hz, 1H). LRMS m/z (rel. int.) 373 (M+, 28.4), 203 (28.9), 115 (35.9), 89 (29.0), 55 (100).

The activated ester 2 was then used to acylate a hexamethyleneamino linking arm that was coupled to the 5' terminus of an oligonucleotide fifteen bases in length. The preparation of the oligonucleotide probe and its linking to the activated ester 2, described in protocol 3, relied on standard procedures of solid phase phosphoramidite chemistry. The final product, a naphthomethylquinone alkylating agent linked probe 3, was then purified by reverse phase chromatography.

Protocol 3, for preparing the oliognucleotides and reaction of the activated ester 2 with oliognucleotide derivatized at the 5'-end with a hexamethyleneamino group All oligonucleotides were synthesized by using standard solid phase cyanoethyl phosphoramidite chemistry on a Dupont CODER 300, (Dupont Inc., Wilmington, Del.) or BioSearch equipment (BioSearch Medical Products, Inc., Somerville, N.J.). The hexamethyleneamino linker was attached during the last step of the synthesis using a monomethoxytrityl protected precursor (a nascent oligonucleotide protected precursor supplied by Clontech, Palo Alto, Calif.) that was designed for the routine protocols of automated synthesis. The protecting group was removed after the completed synthesis by treating the crude oligonucleotide with 80% acetic acid for 30 minutes. The free trityl derivative was extracted by ether. The crude deprotected oligonucleotide was used directly in the final coupling reaction. The activated ester 2 (2.2 mg) was dissolved in 150 μL of DMF and added to the oligonucleotide preparation ($A_{260}$=15.0 absorbance units; ca. 10 absorbance units of amino linked material) dissolved in 150 μL of 0.25M 3-(N-morpholino)-propanesulfonic acid (pH 7.4) and kept undisturbed at 4° C. for 16 hours. Analysis and purification utilized reverse phase HPLC (C-18 Sepherex column) using a gradient of 45 mM triethylamine acetate (pH 6) in 10% $CH_3CN$ to 35 mM triethylamine acetate in 30% acetonitrile in 30 minutes (flow rate=1 mL/min). The methylnaphthoquinone linked probe designated as compound 3, was isolated in 34% yield estimated by the recovery of A260 units.

EXAMPLE 2

Preparation and Coupling of the UV Activated Alkylating Methylnaphthoquinone Linked Probe To A Target Oligonucleotide Strand Target strands of DNA 4, d(AGTGCCACCT-GACGTCTAAG) were prepared in parallel with the alkylating probe 3 of Example 1, and each strand was appropriately labelled with $^{32}P$, in accordance with the procedures described by Maniatis et al., in *J. Molecular Cloning, A Laboratory Manual*, Cold Spring Harbor Laboratory, Cold Spring Harbor, N.Y. (1982), the text of which is incorporated by reference herein.

The target DNA strands 4 and alkylating methylnaphthoquinone probe 3 were annealed and activated under aerobic conditions by irradiating with wavelengths of greater than 345 nm.

Figure 1B:
FIG. 1B shows autoradiograms of denaturing polyacrylamide gels used to identify photochemical crosslinks formed within a duplex DNA structure illustrating one embodiment of the present invention, described in Example 2.
Figure 1C:
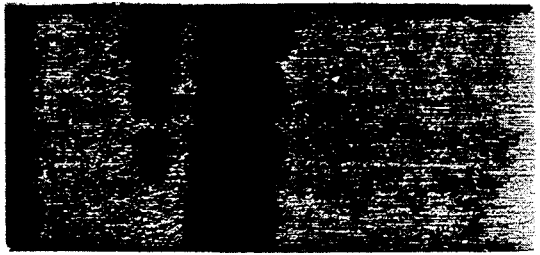
FIG. 1C shows autoradiograms of denaturing polyacrylamide gels used to identify photochemical crosslinks formed within a duplex DNA structure illustrating one embodiment of the present invention, described in Example 2.

FIG. 1 shows autoradiograms of denaturing polyacrylamide (20%) gels which were used to identify the photochemical crosslink formed within the duplex nucleotide structure. In the zone designated as A, the twenty base target DNA strand 4 was labelled at its 5'terminus with $^{32}P$, annealed to the alkylating methylnaphthoquinone linked probe 3, and irradiated for 0.0, 0.5, 1.0 and 5.0 min (lanes 1, 2, 3 and 4) respectively.

In the zone designated as B, the parent nucleotide sequence used to prepare the probe 3 was annealed with labeled target DNA strand 4 and irradiated in the presence of a stoichiometric concentration of the acid 1 for 0.0 and 10 min (lanes 5 and 6). Conversely, this parent oligonucleotide sequence used for preparing the probe 3 was labeled with $^{32}P$ at its 3' terminus, annealed with unlabeled target DNA strand 4 and similarly irradiated in the presence of a stoichiometric concentration of the acid 1 for 0.0 and 10 min (lanes 7 and 8).

In the zone designated as C, the probe 3 was pre-irradiated for 10 minutes, annealed with labeled target DNA strand 4 and further irradiated for 0.0, 5.0 and 10 min (lanes 9, 10 and 11).

In each case, the oligonucleotides (2.2 μM of each strand) were annealed in 1 mM potassium phosphate buffer pH 7 by slowly cooling their heat denatured mixture (65° C.) to ambient temperature over a 3 to 4 hour period. Individual samples (10 L, 10 nCi per lane) were UV activated by placing them in pyrex tubes, screened by a long pass 345 nm filter, at the focal point of a 150 W Xe arc lamp and irradiating for the time periods prescribed above. After photolysis, samples were lyophilized and resuspended in 80% formamide for electrophoresis.

As can be seen from FIG. 1 at Zone A, no oxidative strand scission was detected after the target and reactant strands were annealed, irradiated aerobically under wavelengths of greater than 345 nm and analyzed by electrophoresis (in 7M urea) and autoradiography. Instead, a material migrating more slowly than the 20 base target DNA sequence 4 accumulated over the irradiation times of 0.5, 1 and 5 minutes. This species was evident when a $^{32}P$ label was appended to either the 3' or 5' terminus of the target DNA strand 4 or to the 3' terminus of the probe 3.

Accordingly, the only detectable product of photolysis contained the two complete strands of DNA, i.e. the probe DNA coupled to the target DNA strand, in a nondissociable and likely crosslinked form. This reaction was unique to these photochemical conditions. By contrast, as described below, no similar modification was apparent after treating the annealed complex with heat (90° C., 10 min) or reducing agents.

Irradiation of the untethered mixture of the acid 1 and a duplex formed by the parental probe DNA sequence and the target DNA strand 4, shown in FIG. 1 at Zone B, also lead to no detectable crosslinking or oxidative strand scission. Substituting the target DNA strand 4 with a non-complementary sequence d(CACG-GGAACGCATG) in the above process, did not yield any products evident from autoradiography.

Extensive irradiation of the hybridized complex of the probe 3 and the target DNA sequence 4 never allowed for greater than 20% of a labeled oligonucleotide to convert to a crosslinked structure. Yet, the mixture of modified and unmodified material created during the initial 10 minutes of photolysis persisted unchanged after additional exposure to UV irradiation (over 2 hours). This stability was measured by quantitative anion exchange chromatography (pH 12, Mono Q column (Pharmacia Sweden) but the same trend was visible from the autoradiograph.

Pre-irradiation of the probe 3 prior to hybridization with the target DNA strand 4 dramatically inhibited the formation of any products expected from irradiation of the duplex, as shown in FIG. 1 at Zone C. This suppression of activity would be consistent with a rapid and competing photodegradation of the attached 5-methyl-1,4naphthoquinone when no target is available for alkylation. The formation of the crosslinked material, however, remained unaffected by the presence of the radical trap, mannitol (100 mM), and the substitution of $D_2O$ for $H_2O$. Neither the destruction of the sensitizer not the crosslinking reaction was then dominated by diffusible oxygen species such as hydroxyl radical or $^1O_2$. Either of these intermediates would have been characteristically modulated under these conditions.

Enzymatic and chemical derivation of the crosslinked duplex was used to further describe the nature of this unusual reaction.

Figure 2:
FIG. 2 shows the chemical and enzymatic characterization of the crosslinked duplex formed under UV irradiation of the naphthoquinone alkylating probe and a complementary DNA target strand, as detected by autoradiography after separation using polyacrylamide gel electrophoresis, described in Example 2.

FIG. 2 shows the chemical and enzymatic characterization of the crosslinked duplex formed after irradiation of the crosslinked duplex 3+4, detected by autoradiography after separation by 20% polyacrylamide electrophoresis. Samples were prepared in an identical manner to those prepared for FIG. 1 at Zone A. Duplex DNA was then photolyzed for either 0.0 minutes designated (−), or for 10 minutes designated (+), and subsequently treated as follows:

Lanes 1 and 2—100 mM $\beta$-mercaptoethanol at 37° C. for 30 minutes

Lanes 3 and 4—0.2 mg sodium borohydride dissolved in 10 $\mu$L of 10 mM potassium phosphate buffer pH 8.3 at room temperature for 60 minutes; lyophilized; and, resuspended in 0.2M piperidine formate (pH 2) at 40° C. for 80 minutes.

Lanes 5, 6 and 7—10 units of klenow fragment (BRL), 37° C. for 0, 10 and 30 minutes, respectively.

Lanes 8 and 9—0.2M piperidine formate (pH 2) at 60° C. for 80 minutes; lyophilized; and, resuspended in 0.25M piperidine at 90° C. for 30 minutes.

Lanes 10 and 11—0.25M piperidine at 90° C. for 30 minutes.

Designation of the photochemical product as a crosslinked duplex was confirmed by use of the exonuclease activity exhibited by the Klenow fragment of DNA polymerase I, according to the method described by Cowart et al., in "DNA Substrate Structural Requirements for the Exonuclease and Polymerase Activities of Procaryotic and Phage DNA Polymerases", *Biochemistry*, 28, 1975-1983 (1989). Digestions of this product was quite limited, and unlike the digestion of the non-activated 3+4, i.e. prior to UV irradiation. If photochemical alkylation has occurred at the heteratoms of the nucleotide bases, then treatment by base or acid, as reported by Maxam et al., in "Sequencing End-Labeled DNA with Base-Specific Chemical Cleavages", *Methods in Enzymology*, 65, 499-560 (1980) would have induced the characteristic strand scission.

In contrast, the crosslinked product proved to be no more labile than the unreacted target DNA strand 4 to both the base piperidine and the acid piperidine formate followed by piperidine.

Alternative treatment with $\beta$-mercaptoethanol to displace the thiol linkage of the probe 3 also proved unsuccessful showing that the crosslink is stable to displacement by a thiol. Furthermore, Becker et al., in "Use of light for footprinting DNA in vivo", *Nature*, 309, 682-687 (1984), had shown that acid treatment subsequent to reaction with sodium borohydride resulted in the breakage of the DNA backbone at thymines or cytosines saturated at the 5,6-position. A similar analysis performed on the product generated after irradiation of the crosslinked duplex 3+4 again was insufficient to cause scission at the site of modification.

The surprising stability of this quinone based derivatization leads us to hypothesize an equally unusual bond reorganization and the formation of at least one new carbon-carbon bond. The alkylation process may be reminiscent of a previously characterized dimerization of naphthoquinones reported by Martins et al., in "Photodimerization. Part V. The Conversion of 1,4-Naphthoquinones to 2,2'-Bi[1,4-Naphthoquinonyl] Derivatives Through Photodimerization and Subsequent Photo-Oxidation", *S. Afr. J. Chem.*, 30, 89-93 (1977).

A photochemical reaction uncharacteristic of free 1,4-naphthoquinone can now be induced. Once this molecule is covalently held by a probe in close proximity to a target sequence of DNA. The alkylation, triggered by the irradiation of the linked duplex 3+4, immortalizes the hybridization of this complex.

EXAMPLE 3

Preparation of a Reductively Activated Alkylating Bromomethylnapthoquinonyl Linked Probe (5-Methyl-1,4-naphthoquinonyl thio)-propionic acid 1 is prepared in accordance with protocol 1 of Example 1. The acid 1 is brominated in accordance with protocol 4, described below which is an adaptation of the method of Antonini et al., in *J. Med. Chem.*, 25, (1982) supra.

Protocol 4. for brominating the acid to yield (5-Bromomethyl-1,4-naphthoquinonyl thio)-proprionic acid 1b The acid 1 (59 mmol), N-bromosuccinimide (59 mmol), and azobis (2-methyl-propionitrile) (0.5 g, 3 mmol) is combined in 200 mL of $Ac_2O$ and stirred at 120°-130° C. for about 0.5 hours. When the color lightens, the solution is poured onto ice. The yellow solid is collected and dissolved in $CHCl_3$. The $CHCl_3$ solution is dried using $Na_2SO_4$, concentrated to a small volume, and chromatographed on silica gel column (benzene) to yield the brominated acid (5-bromomethyl-1,4-naphthoquinonyl thio)-proprionic acid, designated as compound 1b.

The brominated acid 1b is then converted to the activated ester 2b and linked to an oligonucleotide probe as described in Example 1 to yield a reductively activated brominated alkylating probe 3b. The bromine leaving group can be substituted in compound 1b or 2b to attach a halogen, or any of the following leaving groups Cl, F, I, OCOR, OH, $OSO_2CH_3$, $OSO_2C_6H_4CH_3$-p, OR, OCONHR, and $OCONHCH_2CH_2R$. The procedure is described in the following protocols 5-11 which are adapted from Antonini et al., (1982) supra, incorporated by reference herein, to form substituted acids (1c-1i) or substituted esters (2c-2i). The substituted acids (1c-1i) can then be converted to the activated esters (2c-2i) and attached to the probe as described in Example 1.

Protocol 5, for replacing the bromine with an Acetoxy (OAC) leaving group to yield (5-Acetoxymethyl-1,4-naphthoquinonyl thio)-propionic acid 1c A mixture of the brominated acid 1b (6 mmol) and silver acetate (2.2 g, 13.2 mmol) is combined in 20 mL of $CHCl_3$ and 40 mL of AcOH, heated at 95° to 100° C. with vigorous stirring overnight. The solvent was evaporated in vacuo, and the residue was poured onto ice water saturated with NaCl. The crude product and AgCl were collected by filtration and washed with water. The solid was then added to a $CHCl_3$, and the insoluble AgCl was removed by filtration. The AgCl was washed with $CHCl_3$ until the washings were colorless. The combined $CHCl_3$ solutions were dried with $Na_2SO_4$, concentrated and chromatographed on a silica gel column ($C_6H_6$-$CHCl_3$, 1:1, v/v). To yield (5-acetoxymethyl-1,4-naphthoquinonyl thio)-propionic acid, designated 1c.

Protocol 6, for replacing the bromine with an Hydroxy (OH) leaving group to yield (5-hydroxymethyl-1,4-naphthoquinonyl thio)-propionic acid 1d The bromomethyl acid 1b (6 mmol) is mixed in 50 mL of water-dioxane (3:2, v/v) and refluxed with stirring for 1 hour. The solution is then diluted with water (300 mL) and extracted with $CHCl_3$ (3×300 mL). The $CHCl_3$ solution is dried ($Na_2SO_4$), concentrated, and chromatographed on a silica gel column ($CHCl_3$-EtOAc, 7:3 v/v) to yield (5-hydroxymethyl-1,4-naphthoquinonyl thio)-propionic acid, designated 1d.

Protocol 7, for replacing the bromine with a (methanesulfonyl)-oxy ($OSO_2CH_3$) leaving group to yield the (5-[[(methanesulfonyl)oxy]methyl]-1,4-naphthoquinonyl thio)-propionic acid 1e The bromomethyl acid 1b (6 mmol) and silver methanesulfonate (4.8 g, 24 mmol) are combined in 30 mL of $CH_3CN$ and stirred at room temperature for 6 hours. (5-[[(methanesulfonyl)oxy]methyl]-1,4-naphthoquinonyl thio)propionic acid, designated 1e is isolated by evaporating the solvent in vacuo at 40° C. and extracting the residue with $CHCl_3$ (5×50 mL). The combined $CHCl_3$ extracts are concentrated and chromatographed on a silica gel column (benzene-EtOAc, 9:1, v/v) to yield compound 1e.

Protocol 8, for replacing the bromine with a Toluenesulfonyl) oxy]($OSO_2C_6H_4CH_3$-p) leaving group to yield (5-[[(p-toluenesulfonyl)oxy]methyl]-1,4-naphthoquinonyl thio)-proprionic acid 1f The bromomethyl acid 1b (4.0 mmol) is combined with silver p-toluenesulfonate (4.5 g, 16 mmol) and 25 mL of $CH_3CN$ and stirred at room temperature overnight. The solvent is evaporated to dryness under reduced pressure at 40° C. The residue is then extracted with $CHCl_3$(5×50 mL), and the combined $CHCl_3$ solution is concentrated to a small volume and chromatographed on a silica gel column ($CHCl_3$) to yield (5-[[(p-toluenesulfonyl)oxy]methyl]-1,4-naphthoquinonyl thio)-propionic acid, designated 1f.

Protocol 9, for replacing the bromine with an ethoxymethyl ($OCH_2CH_3$) leaving group to yield 5-(ethoxymethyl)-1,4-naphthoquinonyl thio)-propionic acid 1g The bromomethyl acid 1g (2.0 mmol) is combined in a mixture of EtOH and $H_2O$ (4:1, v/v) and refluxed for 2 hours. The solution is poured onto ice, and the yellow precipitate that forms is collected by filtration. The crude product is dissolved in $CHCl_3$, dried ($Na_2SO_4$), concentrated to a small volume, and chromatographed on a silica gel column (benzene-EtOAc, 4:1, v/v). The pure product 5-(ethoxymethyl)-1,4-naphthoquinonyl thio)-propionic acid, designated 1g is then isolated.

Protocol 10, for inserting a hydroxy(N-methylcarbamate) ($OCONHCH_3$) leaving group to yield 5-(hydroxymethyl)-1,4-naphthoquinonyl N-methyl)-thio]-propionic acid 1h Methyl isocyanate (35 mL) is added to a solution of the Hydroxymethyl acid 1d (4.8 mmol) prepared according to Protocol 6, in 25 mL of $CHCl_3$. The solution is refluxed with stirring for 30 hours and then evaporated to dryness under reduced pressure. The residue is crystallized from $CHCl_3$-EtOAc to yield 5-[(hydroxymethyl)-1,4-naphthoquinonyl N-methyl)-thio]-propionic acid, designated 1h. The mother liquor is concentrated and chromatographed on a silica gel column ($CHCl_3$ EtOAc, 4:1, v/v) to afford additional recovery of 1h.

Protocol 11, for inserting a hydroxy N-chloroethyl)carbamate ($OCONHCH_2CH_2Cl$) leaving group to yield 5-[hydroxymethyl-1,4-naphthoquinonyl N-(chloroethyl)carbamate)-thio]propionic acid 1i Chloroethyl isocyanate (35 mL) is added to a solution of the Hydroxymethyl acid 1d (4.3 mmol), prepared according to Protocol 6, in $CHCl_3$ (18 mL). The reaction mixture is refluxed with stirring for 6 hours, and concentrated in vacuo to dryness at 50° C. The residue is then dissolved in a small amount of $CHCl_3$ and chromatographed on a silica gel column ($CHCl_3$) to yield 5-[(hydroxymethyl-1,4-naphthoquinonyl N-(chloroethyl)carbamate)thio]-propionic acid, designated 1i.

All of these compounds, 1b through 1i, may then be modified to the activated ester, as described in Example 1 at Protocol 2, to yield the naphthoquinone thio esters 2b through 2i, respectively. The probe molecule is then attached, as described in Example 1 at Protocol 3, to yield compounds 3b through 3i, respectively. If the probe is an oligonucleotide, then it may be attached to the respective naphthoquinone thio esters 2b through 2i at either its 5' or 3' terminus. Alternatively, the oligonucleotide may be linked to naphthoquinone thio esters 2b through 2i, respectively, at any oligonucleotide base or phosphoribose backbone suitably modified in accordance to the methods described by the following publications, the disclosure of which is incorporated by reference herein:

1. Gebeyehu et al., "Novel Biotinylated nucleotide-analogs for labelling and colorimetric detection of DNA", Nucl Acids Res., 15, 4513-4534 (1987).
2. Jäger et al., "Oligonucleotide N-alkylphosphotamides: Synthesis and Binding to Polynucleotides", Biochemistry, 27, 7237-7246 (1988).
3. Cocuzza, "Total Synthesis of 7-Iodo-2',3'-Dideoxy-7-deazapurine Nucleosides, Key intermediates in the Preparation of Reagents for the Automated Sequencing of DNA", Tetra. Letts., 29, 4061-4064 (1988).
4. Hanna et al., "Synthesis and Characterization of 5-[(4-Azidophenacyl)thio]uridine 5'-Triphosphate, a Cleavable Photo-Cross-Linking Nucleotide Analogue", Biochemistry, 28, 5814-5820 (1989).
5. Gibson et al., "Synthesis and Application of Derivatizable Oligonucleotides", Nucl Acids Res., 15, 6455-6467 (1987).

The compounds 3b through 3i, described above, are introduced to the target molecule, such as DNA in vitro. If in vivo use is desired, then suitably modified probes that are capable of transversing cell membranes are prepared, for example as described by Blake et al., "Hybridization Arrest of Globin Synthesis in Rabbit Reticulocyte Lysates and Cells by Oligodeoxyribonucleoside Methylphosphonates", Biochemistry, 24, 6139-6145 (1985); and, by Agrawal et al., "Oligodeoxynucleoside Phosphoramidates and Phosphorothioates as Inhibitors of Human Immunodeficiency Virus", Proc.

Nat'l. Acad. Sci. U.S.A., 7079-7083 (1988). These probes are then attached to activated esters 2b-2i, respectively.

After the probes are introduced to the target molecule, they are then reductively activated for forming a covalent bond to the target oligonucleotide in close proximity to the hybridization site of the probe and target oligonucleotides. The reductive signal for activating covalent binding initiated by the alkyl linked leaving group in vivo may be a reducing enzyme of a particular media or cell, or an externally introduced reductive signal. In vitro activation may be initiated by various reducing agents such as sodium borohydride, dithionite, sodium cyanoborohydride, and thiols. The naturally occurring reducing agent, or externally introduced reductive signal causes covalent bonding between a methylene group and the target oligonucleotide. The general mechanism of the reductive activation and alkylation is adapted from the scheme described by Antonini et al., (1982) supra, and is generally outlined in scheme 2, which is illustrated in FIG. 3.

EXAMPLE 4

Figure 3:
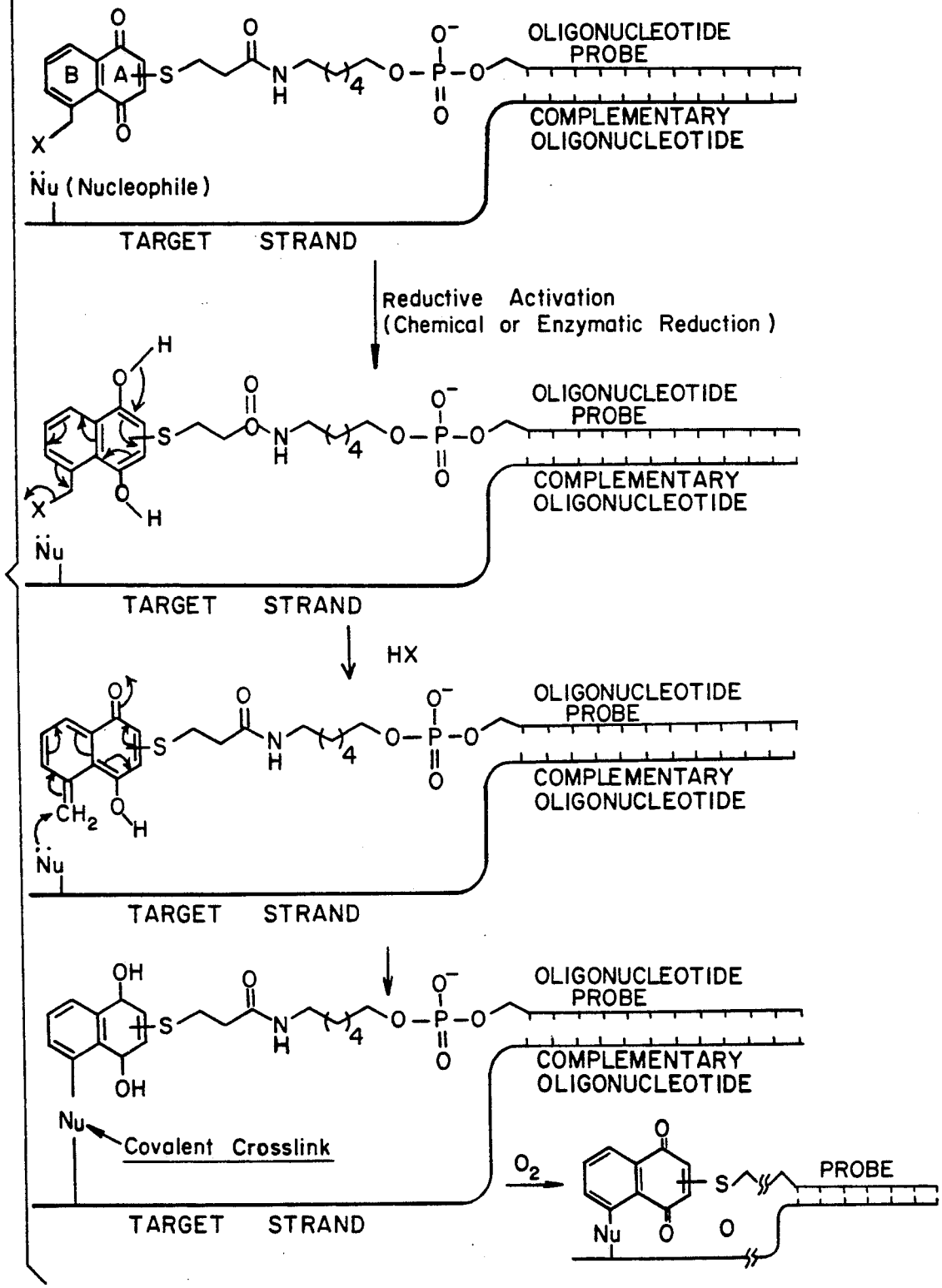
FIG. 3 illustrates Scheme 2 for the reductive activation and alkylation of a target oligonucleotide by each of the alkylating naphthoquinone probes (3b–3i), respectively, as described in Example 3.

As can be seen in Scheme 2 which is illustrated in FIG. 3, the alkyl $R_4$ leaving group is always attached to the B ring. Attachment of the alkyl $R_4$ leaving group to the A ring makes the compound too reactive, causing it to attack and degrade the probe oligonucleotide strand during the linking step. The criticality of attaching the alkyl $R_4$ leaving group to the B ring was never appreciated by Antonini et al., who showed the chemistry of these compounds to be interchangeable, see Scheme I of Antonini et al. at page 731, (1982) supra.

In this experiment, 2-bromomethyl-1,4-naphthoquinonyl thio)-propionic acid was prepared, as described in Example 3, esterified, and linked to the oligonucleotide probe, as described in Example 1.

The modified oligonucleotide, described in Example 2, $A_{260}=0.20$ units) was treated in 5μL 0.25M 3-(N-morpholino)-propanesulfonic acid (MOPS) (pH 7.4) with the bromomethyl N-hydroxysuccinimide ester (0.2 mg, over 100 fold excess) in 5μL di-methylformamide (DMF) and analyzed on a Sepherex reverse phase C-18 column using a gradient of 46mM tri-ethyl ammonium acetate (TEAA) (pH 7) in 8% acetonitrile to 42 mM TEAA in 16% acetonitrile in 30 minutes. A loss of the modified probe oligonucleotide peak eluting at 16 minutes was observed after 2 hours. Two additional peaks were seen eluting at 24 and 33 minutes. A controlled reaction with MOPS and a bromomethyl naphthoquinone succinimide ester showed that the peaks appearing at 24 and 33 minutes were decomposition products of the bromomethyl naphthoquinone succinimide ester. Another control reaction with non-complementary fragments of DNA in MOPS and bromomethyl naphthoquinone succinimide ester showed the disappearance of the starting material peak at 16 minutes within two hours, as well as the appearance of additional peaks at 24 and 33 minutes. Since no other oligonucleotide peaks were observed, the oligonucleotide must have either, (a) be precipitating on the column, or
(b) being randomly linked to the bromomethyl succinimide ester via the nucleophilic groups on the oligonucleotide bases. This hypothesis is based on the fact that the bromo groups can be easily displaced by nucleophiles.

Random attachment to the oligonucleotide would result in very small concentration of a large number of species eluting at different times on the column, resulting in the disappearance the starting material peak with no other peak being evident. Since the second possibility seems more likely, the synthesis of a derivative with a less labile leaving group R4 is necessary. This would reduce the possibility of nucleophiles on the oligonucleotide displacing the hydroxy group (poor leaving group), as well as increase the probability of the amino group on the modified oligonucleotide strand reacting with a N-hydroxy succinimide ester of (2-hydroxymethyl-1,4-naphthoquinonyl thio)-propionic acid to form a covalent linkage. However, the other leaving groups attached adjacent to the A ring were found to be equally reactive. Accordingly, we have concluded that the methyl-leaving group, $-CH_2-X$, may only be placed on the B ring to allow linking with the probe.

Thus, while we have described what are presently the preferred embodiments of the present invention, other and further changes and modifications could be made thereto without departing from the scope of the invention, and it is intended by the inventors herein to claim all such changes and modifications.

We claim:

1. A naphthoquinone probe for covalently bonding a nucleic acid target molecule in response to photochemical activation by light irradiation, the naphthoquinone probe having the formula:

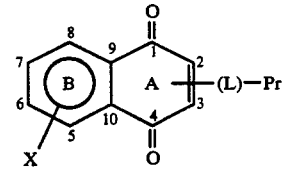

wherein X is a methyl group, and X is positioned on nay of carbon atoms 2-3 and 5-8, wherein said methyl group is capable of alkylation of and covalent bonding to a nucleic acid target molecule due to photochemical activation by light irradiation of the naphthoquinone probe; wherein L is an N-hydroxy succinimide ester linking group for attaching a probe that localizes to nucleic acid to either ring A or ring B; and wherein Pr is a nucleic acid probe that preferably localizes to nucleic acid for binding to a nucleic acid target molecule.

2. A naphthoquinone probe according to claim 1, wherein Pr is a DNA strand.

3. A naphthoquinone probe according to claim 1, wherein Pr is a RNA strand.

4. A naphthoquinone probe according to claim 1, wherein said nucleic acid is linked to L by its 5' terminus.

5. A naphthoquinone probe according to claim 1, wherein said nucleic acid is linked to L by its 5' terminus.

6. A naphthoquinone probe for selectively covalently bonding to a nucleic acid target molecule in response to activation by a reductive signal, the naphthoquinone probe having the formula:

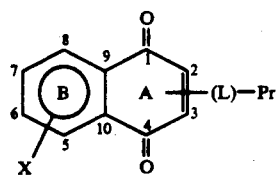

wherein X is located at any of carbon atoms 5–8 of the B ring, and X is selected from the group consisting of $CH_2Br$, $CH_2Cl$, $CH_2F$, $CH_2I$, $CH_2OAc$, $CH_2OH$, $CH_2OSO_2CH_3$, $CH_2OSO_2C_6H_4CH_3$-p, $CH_2OCH_2CH_3$, $CH_2OCONHCH_3$ and $CH_2OCONHCH_2CH_2Cl$;

wherein L is an N-hydroxy succinimide ester linking group for attaching a nucleic acid probe to either ring A or ring B; and wherein Pr is a nucleic acid probe that preferably localizes to a nucleic acid molecule for binding to a nucleic acid target molecule.

7. A naphthoquinone probe according to claim 6, wherein Pr is a DNA strand.

8. A naphthoquinone probe according to claim 6, wherein Pr is a RNA strand.

9. A naphthoquinone probe according to claim 6, wherein said nucleic acid is linked to L by its 5' terminus.

10. A naphthoquinone probe according to claim 6, wherein said nucleic acid is linked to L by its 3' terminus.

11. A naphthoquinone probe according to claim 6, wherein X is $CH_2Br$.

* * * * *

UNITED STATES PATENT AND TRADEMARK OFFICE
CERTIFICATE OF CORRECTION

PATENT NO. : 5,292,873
DATED : March 8, 1994
INVENTOR(S) : Rokita, et. al.

It is certified that error appears in the above-indentified patent and that said Letters Patent is hereby corrected as shown below:

| | |
|---|---|
| In Column 1, Line 30, | now reads "hydridization", should read --hybridization--; |
| In Column 2, Line 32, | now reads "5+-linked", should read --5'-linked--; |
| In Column 7, Line 49, and 50, | now reads "linking step derivative", should read --linking step includes a step of adapting the 1,4-naphthoquinone derivative--; |
| In Column 8, Line 33, | now reads "2a-2i", should read --2b-2i--; |
| In Column 8, Line 37, | now reads "reported by et al.(1982)", should read --reported by Antonini et al. (1982)--; |

UNITED STATES PATENT AND TRADEMARK OFFICE
CERTIFICATE OF CORRECTION

Page 2 of 3

PATENT NO. : 5,292,873
DATED : March 8, 1994
INVENTOR(S) : Rokita, et. al.

It is certified that error appears in the above-indentified patent and that said Letters Patent is hereby corrected as shown below:

| | |
|---|---|
| In Column 9, Line 39, | now reads "yield 5-methyl", should read --yield (5-methyl--; |
| In Column 12, Line 12, | now reads "(10 L. 10)", should read --(10 µL. 10 nCi per lane)--. |
| Line 64, | now reads "1,4 naphthoquinone", should read --1,4-naphthoquinone--; |
| In Column 14, Line 22, | now reads "acid to", should read --acid 1 to--; |
| In Column 15, Line 21, | now reads "acid 1e", should read --acid 1e:--, |
| Line 33, | now reads "Toluenesulfonyl)oxy], should read --[p-Toluenesulfonyl)oxy]--; |

UNITED STATES PATENT AND TRADEMARK OFFICE
CERTIFICATE OF CORRECTION

PATENT NO. : 5,292,873
DATED : March 4, 1994
INVENTOR(S) : Rokita, et. al.

It is certified that error appears in the above-indentified patent and that said Letters Patent is hereby corrected as shown below:

|  |  |
|---|---|
| Line 37, | now reads "acid 1*f*", should read --acid 1*f*:--; |
| Line 52, | now reads "acid 1*g*", should read --acid 1*g*:--; |
| Line 65, | now reads "yield 5 - (hydroxymethyl", should read --yield 5-[(hydroxymethyl--; |
| Line 66, | now reads "acid 1*h*", should read --acid 1*h*:--; |
| In Column 16, Line 15, | now reads "acid 1*i*", should read --acid 1*i*:--; |
| In Column 17, Line 1, | now reads "U.S.A., 7079", should read --"*U.S.A.*, 85,7079--; |

Signed and Sealed this

Twentieth Day of June, 1995

Attest:

BRUCE LEHMAN

Attesting Officer        Commissioner of Patents and Trademarks